United States Patent [19]

Forrest et al.

[11] Patent Number: 4,778,769
[45] Date of Patent: Oct. 18, 1988

[54] METHODS OF ELECTROCHEMICAL ASSAY EMPLOYING A FIELD EFFECT TRANSISTOR

[75] Inventors: Gordon C. Forrest; Simon J. Rattle; Grenville A. Robinson, all of Great Britain

[73] Assignee: Serono Diagnostics Ltd., Great Britain

[21] Appl. No.: 712,193

[22] Filed: Mar. 15, 1985

[30] Foreign Application Priority Data

Mar. 16, 1984 [GB] United Kingdom ............... 8406955

[51] Int. Cl.$^4$ ............... G01N 33/551; G01N 33/552; G01N 33/553; G01N 33/557
[52] U.S. Cl. ............... 436/501; 204/403; 204/416; 357/25; 435/176; 435/817; 436/517; 436/524; 436/525; 436/527; 436/806; 436/807
[58] Field of Search ............... 436/524, 806, 525, 527, 436/501, 807, 517; 530/811; 204/403, 416; 357/25; 435/176, 817

[56] References Cited

U.S. PATENT DOCUMENTS

| | | | |
|---|---|---|---|
| 4,020,830 | 5/1977 | Johnson et al. | 204/403 |
| 4,238,757 | 12/1980 | Schenck | 436/806 |
| 4,273,636 | 6/1981 | Shimada et al. | 357/25 |
| 4,411,741 | 10/1983 | Janata | 357/25 |
| 4,437,969 | 3/1984 | Covington et al. | 204/403 |

FOREIGN PATENT DOCUMENTS 1130378 3/1980 Canada .

OTHER PUBLICATIONS

Naoto Yamamoto, et al., "Antigen-Antibody Reaction Investigated with Use of a Chemically Modified Electrode", Clinical Chemistry, vol. 26, No. 11, 1980, pp. 1569-1572.

*Primary Examiner*—Robert J. Warden
*Assistant Examiner*—David A. Saunders
*Attorney, Agent, or Firm*—Ostrolenk, Faber, Gerb & Soffen

[57] ABSTRACT

In its broadest aspect, the present invention provides a method of assaying a ligand in a sample which comprises contacting the sample with a predetermined quantity of a specific binding partner to the ligand, said specific binding partner being immobilized on the effective gate electrode of a field effect transistor, and determining whether (and, if desired, the extent to which) an appropriate transistor characteristic is changed as a result of complex formation between the ligand and the specific binding partner.

10 Claims, 3 Drawing Sheets

$$\Delta V_{out} = \Delta V_g$$

METHODS OF ELECTROCHEMICAL ASSAY EMPLOYING A FIELD EFFECT TRANSISTOR

The present invention relates to methods of assaying one of a pair of specific binding partners, and to apparatus for carrying out these methods.

There is today a great need for rapid and accurate methods of assaying biologically active substances (which may be at low concentrations), particularly in body fluids such as blood, saliva or urine. A wide variety of medical conditions such as pregnancy, drug overdose, metabolic birth defects, hormonal disorders and diabetes can be diagnosed using such assay techniques.

Many assay methods rely on the formation of a complex between the species under assay (hereinafter called "ligand") and another species to which it will bind specifically (hereinafter called "specific binding partner"). The extent of complex formation is a function of the amount of the ligand present.

The assay of ligand is determined by monitoring the extent of complex formation, for example by use of chemical or biochemical labels. Several methods of labelling have been employed, for example labelling employing radioisotopic, fluoroescent or bioluminescent species, spin-labelling or enzyme labelling.

The use of radioisotopic labels has become particularly widespread, due to the high degree of sensitivity and specificity obtainable.

There are, however, disadvantages to the use of radioactive labels. They have limited shelf-life due to spontaneous decay, necessitating frequent recalibration of the equipment, and their use will require adherence to strict safety precautions and is subject to legal regulation. These disadvantages will inevitably lead to higher costs and the necessity for high standards of sophistication of equipment, laboratory facilities and personnel.

An alternative label which has been employed is an enzyme label. In such methods, the enzyme label is monitored for example by measuring the removal of substrate or the appearance of the product of the enzyme-catalysed substrate reaction by spectrophotometry, nephelometry, fluorimetry or by radiometry.

Such monitoring techniques may lack the high degree of sensitivity and specificity required for modern assay work. This may be due to the fact that neither the primary nor the secondary reaction is 100% quantitative or there may be inaccuracy in end-point assessment. The use of radioactive labels presents the usual problems of safety and short shelf-life of the reagents. The chromogens used in spectrophotometric techniques are often carcinogenic.

In general, the apparatus used with known assay methods of the types mentioned above is not suitable for miniaturisation. The methods thus require relatively large amounts of inconvenient or even dangerous reagents and the apparatus tends to be bulky and expensive.

It is one of the objects of the present invention to overcome these disadvantages and to provide a new assay method which is sensitive, specific and convenient and which does not require the use of labelled reagents, and an apparatus for carrying out such a method which may be suitable for miniaturisation.

We have now found that certain microelectronic devices, in particular field effect transistors (FET's), may be employed in assay methods to provide a cheap and robust system, suitable for miniaturisation, which does not require labelled reagents.

Thus, in its broadest aspect, the invention provides a method of assaying a ligand selected from antigens and antibodies in a sample, which comprises contacting the sample with a predetermined quantity of a specific binding partner (an antigen or antibody) to the ligand, said specific binding partner being immobilised on and effective gate electrode of a field effect transistor, said gate electrode being spatially separate from the other components of the field effect transistor and determining whether (and, if desired, the extent to which) an appropriate transistor characteristic is changed as a result of complex formation between the ligand and the specific binding partner.

The assay can be completed from the determined change in the transistor characteristic with reference to calibration data.

The method of the present invention is applicable both to qualitative and to quantitative assays.

DESCRIPTION OF THE PREFERRED EMBODIMENTS

Figure 1:
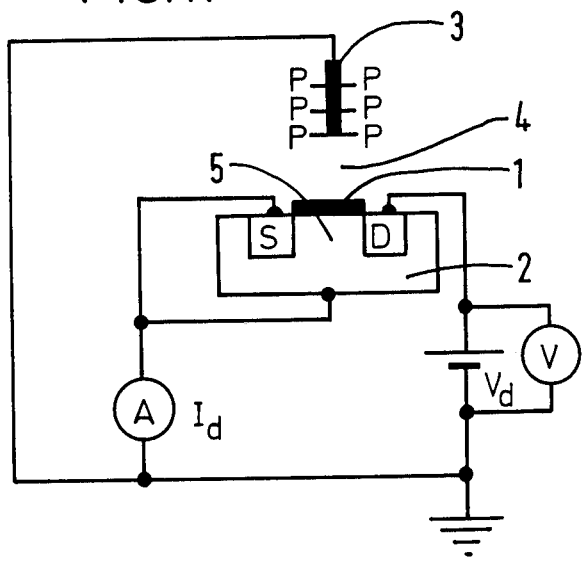
FIG. 1 is a schematic representation of a first embodiment of the invention.
Figure 2:
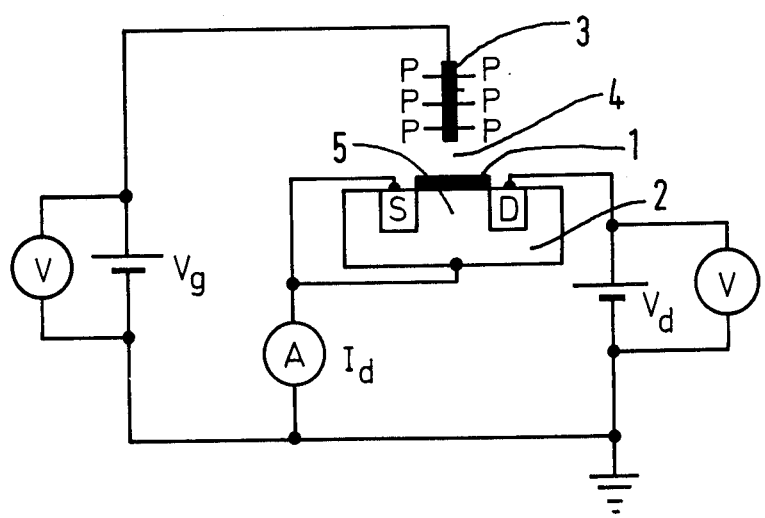
FIG. 2 is a schematic representation of a second embodiment of the invention.
Figure 3:
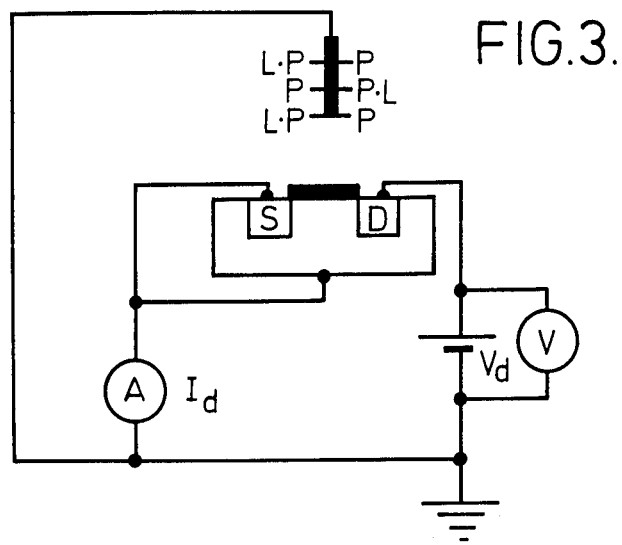
FIG. 3 is a schematic representation of the first embodiment after complex formation.
Figure 4:
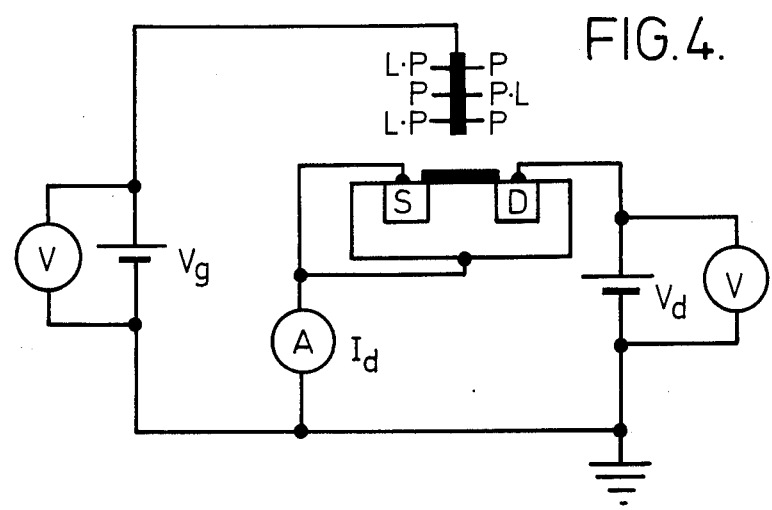
FIG. 4 is a schematic representation of the second embodiment after complex formation.
Figure 5:
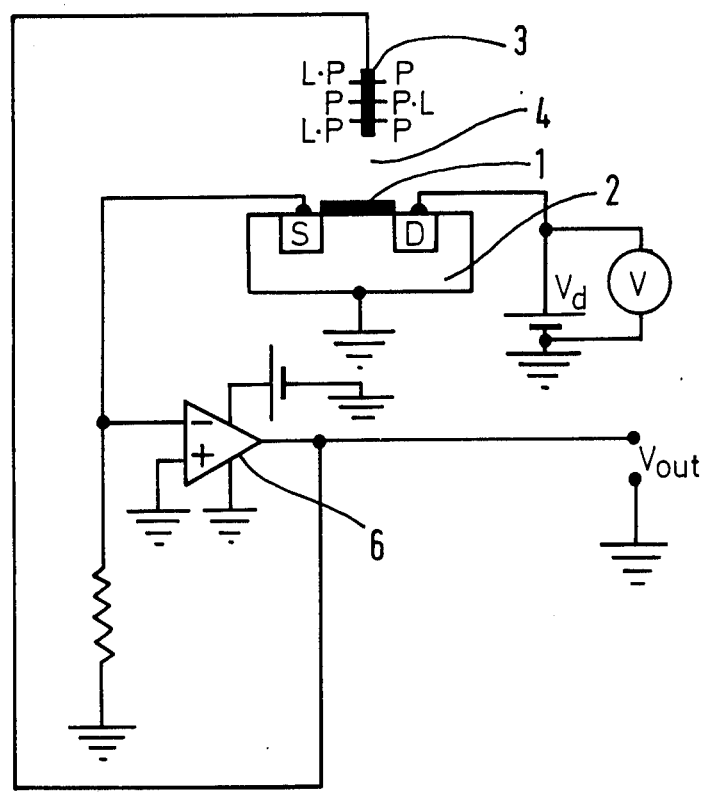
FIG. 5 is a schematic representation of a third embodiment of the invention.

The term "effective gate electrode" used herein refers to an electrode functioning as the gate electrode of the FET. It will be appreciated that the construction of an effective gate electrode may differ considerably from that of conventional gate electrodes. The construction of effective gate electrodes is described below.

As stated above, a predetermined quantity of a specific binding partner is immobilised on the effective gate electrode. The specific binding partner may be present in a quantity greater than, equivalent to or less than the quantity of ligand present in the sample.

The change in the transistor characteristic may be determined as an absolute change observed after the complexing reaction has been allowed to proceed for a controlled period of time, or a rate of change of that characteristic with respect to time. In the second alternative, the initial rate of change may conveniently be measured. The method used will always, however, be consistent with the method employed in the calibration experiments. In the "absolute" mode, the specific binding partner will typically be present in a quantity greater than or equivalent to the quantity of ligand present in the sample. In the "rate" mode, the specific binding partner may be present in a quantity greater than, equivalent to or less than the quantity of ligand present in the sample.

Apparatus for carrying out the method of invention, comprising an FET, effective gate electrode and associated electrical circuit, are shown in diagrammatic form in the accompanying drawings. A gate insulator 1 (preferably ion-insensitive) of insulating material [e.g. silicon dioxide, silicon nitride (which may for example have been treated with sodium hydroxide to reduce pH sensitivity) or paralene (which may for example have been deposited under vacuum thereby giving an ion-insensitive (FET)] approximately 1000 Å in thickness covers the surface of a p-type silicon substrate 2 between two diffusions of n-type silicon (the 'source' area S and 'drain' area D). An effective gate electrode 3 on which is immobilised a predetermined quantity of the specific binding partner P lies over the gate insulator and an electrolyte 4 is present in contact with the electrode and the insulator.

When the gate electrode is at or below the threshold potential ($V_T$) of the device there is insignificant flow of electric current between the S and D areas since no electrons can pass from the n-type source area to the p-type substrate. A suitable device may have a $V_T$ of approximately $-0.5$ V. When the gate electrode potential $V_g$ is greater than $V_T$ (see FIGS. I and II), an electric field is generated across the gate insulator, which causes repulsion of the majority p-type carriers from the gate insulator/substrate interface, forming a depletion region 5 between the source and drain areas where negative carriers predominate. On applying a potential $V_d$ (the drain voltage) between the S and D areas, a drain current $I_d$ will flow.

The threshold potential $V_T$ of the FET will vary with individual devices. It can have a value of zero or can have a positive or negative non-zero value. As mentioned above, a suitable FET for use in the present invention may have a $V_T$ of approximately $-0.5$ V so that the device may be "on" without the immobilised specific binding partner being subjected to a large local electric field.

Complex formation between the ligand L and the immobilised specific binding partner on addition of the sample (see FIGS. III and IV) may cause a change in a transistor characteristic. Without wishing to be bound by theoretical considerations, we believe that this may be due to a redistribution of, and change in, electrical charge in one or both of the complexing partners. Such a change is quantitative and is a measure of the extent of complex formation, thereby being dependent on the amount of ligand in the sample under assay. The change will be observable as a change in the drain current $I_d$ or the gate electrode potential $V_g$.

Thus, if one of the characteristics $I_d$ and $V_g$ is held constant, any change in the other characteristic will be due directly to complex formation between the specific binding partner and the ligand under assay. If in addition, the parameters of $V_d$, pH, ionic strength and temperature are maintained constant and/or variations therein compensated for, such a change will be due solely to complex formation. The pH may, for example, be controlled by the use of buffers.

In the apparatus shown in FIGS. III and IV, the change in the drain current $I_d$ on addition of the sample to be assayed is monitored at the current meter A with respectively zero and non-zero constant $V_g$ (in both cases, $V_g$ being greater than $V_T$). Alternatively, however, a system may be employed in which the FET is used in conjunction with an Operational Amplifier 6 (see FIG. V) and the change in the gate electrode potential $V_g$ needed to maintain a constant $I_d$ is monitored as a function of the change in the output voltage $V_{out}$ of the Operational Amplifier using a feedback circuit.

According to one feature of the present invention, therefore, there is provided a method of assay as herein described wherein the change in one transistor characteristic selected from the drain current characteristic and the gate electrode potential characteristic as a result of complex formation is determined, the other characteristic and optionally also the drain potential $V_d$, the pH and ionic strength of the assay medium and the temperature of the system being maintained constant or variations therein compensated for.

The nature of the effective gate electrode may be varied to suit the assay conditions. Particularly suitable for the assays of the present invention is a titanium dioxide gate electrode which may be chemically activated to permit coupling with the specific binding partner. Alternatively, a conventional glass-bodied calomel electrode, a Ag/AgCl electrode, or any other suitable gate electrode may be used. Techniques for immobilising specific binding partners to glass and metal oxide surfaces are well-known in the art.

It may prove advantageous to use a reference electrode to permit compensation for non-specific binding of other non-ligand species present in the sample with the electrode-immobilised reagent and/or for variations in $V_d$, pH, ionic strength and temperature. Such a reference electrode may act as a secondary gate electrode or may be used with a second FET, the outputs of the two transistors being monitored differentially. If appropriate, such an electrode may be chemically activated in an analagous way to the primary gate electrode, although not carrying specific binding partner. Furthermore, non-specific effects may be reduced by the covering the electrode bearing the immobilised specific binding partner with a membrane which is either permeable to, or perm-selective for, the ligand under assay. The reference system may also be protected by such a membrane.

According to a further feature of the present invention, therefore, there is provided apparatus for carrying out the assay methods as herein described, which apparatus includes a field effect transistor, the effective gate electrode of which has the specific binding partner immobilised thereon, and optionally a reference electrode. An aqueous assay medium may be present, comprising a suitable pH buffer, which may advantageously act as an electrolyte. Means may be provided for incubating the assay mixture at any desired temperature. The aqueous assay medium and the sample to be assayed may conveniently be introduced in any desired order through an entry port provided in the apparatus. The apparatus will generally further comprise a suitable electrical circuit.

Advantageously the apparatus may be pre-calibrated and provided with a scale whereby the change in the appropriate transistor characteristic may be read off directly as an amount of ligand in the sample.

Conventional means may be employed to minimise channel current noise and hence increase the sensitivity of the method.

The method of the invention is particularly suitable for assaying the following ligands: Hormones, including peptide hormones (e.g. thyroid stimulating hormone (TSH), lutenising hormone (LH), follicle stimulating hormone (FSH) human charionic gonadatraphin (HCG), insulin and prolactin) and non-peptide hormones (such as thyroxine and tri-iodothyronine), proteins, including carcinoembryonic antigen (CEA) and alphafetoprotein (AFP), drugs (e.g. digoxin), sugars, toxins and vitamins.

It will be understood that the term "antibody" used herein includes within its scope (a) any of the various sub-classes of immunoglobulin, e.g. IgG, IgM, derived from any of the animals conventionally used, e.g. sheep, rabbits, goats or mice, (b) monoclonal antibodies, (c) intact molecules or "fragment" of antibodies, monoclonal or polyclonal, the fragments being those which contain the binding region of the antibody, i.e. fragments devoid of the Fc portion (e.g., Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacteria fragments, cells, cell fragments and viruses) and haptens which may be rendered antigenic under suitable conditions.

Immobilisation of an antibody or antigen molecule onto a gate electrode may be effected by various methods. The attachment of the antibody or antigen to the electrode can be via any portion of the molecular structure so long as specific immunological activity is retained at the antibody or antigen binding site.

The electrode and/or the antibody or antigen may be chemically modified to permit successful attachment. For example, a titanium dioxide electrode carrying immobilised antibody may be prepared by heating a titanium wire at about 1000° C. to form a thin oxide layer on its surface, contacting it firstly with a basic solution of cyanogen bromide and then with a basic solution of the antibody, and finally deactivating with urea the remaining active sites which have not taken up antibody. In another method, a titanium dioxide electrode carrying immobilised protein (e.g. an enzyme such as glucose oxidase) may be prepared by heating a titanium wire at about 900°–1000° C. and allowing it to cool to form a thin titanium dioxide layer on its surface, silanising it (for example by contacting with a solution of γ-aminopropyltriethoxysilane in an appropriate solvent, e.g. acetone and subsequently evaporating the solvent) and then contacting it with firstly a solution of glutaraldehyde and secondly with a solution of the protein, and finally washing and deactivating the remaining active sites with urea. A reference electrode may be prepared in analogous ways but omitting the stage of contacting the wire with the solution of the antibody or protein.

Electrode-immobilisation of an antibody or antigen reagent may also for example be achieved by bonding interactions between functional groups on the antibody or antigen molecule and the electrode, or by cross-linking or adsorption onto the surface of the electrode. Binding of reagents to the electrode may generally be accomplished by methods analogous to known methods of binding such reagents to solid supports (e.g. particles and beads), for example those described in European patent application No. 83305834.0.

The magnitude of the change in transistor characteristic due to complexing between an antibody and antigen will typically be of the order of millivolts or milliamperes. The magnitude may vary due, inter alia, to the particular electrode used, the pH of the medium, the purity of the reagent used on the electrode and the ionic strength of the medium, and such parameters must therefore be consistent between the calibration experiments and the assay methods.

The following non-limiting Example is intended to illustrate the invention more fully.

EXAMPLE 1

Attachment of Enzymes to a titanium dioxide electrode

Titanium rods (2 cm long × 0.2 cm diameter) were heated for 12 hours at +900° C. and then allowed to cool overnight, thus growing a thin layer of titanium dioxide on the surface.

Silanisation of the rods was achieved by adding them to a 1% (v/v) solution of γ-aminopropyltriethoxysilane in acetone and evaporating to dryness. The rods were then baked at 80° C. for 22 hours.

The rods were soaked in a 2.5% (v/v) solution of glutaraldehyde in phosphate buffer (50 mM, pH 7.4) for 2½ hours at 25° C. After thorough washing with deionised water, the rods were contacted with a solution of glucose oxidase (0.33 mg/ml in phosphate buffer, 50 mM, pH 7.4) overnight at 4° C. After thorough washing with deionised water and soaking with 6M urea to remove any adsorbed enzyme, the rods were assayed for glucose oxidase activity.

A control rod was produced by following the above procedure but not contacting the rod with glucose oxidase.

| Results | Enzyme activity (International Units) |
|---|---|
| ROD 1 | $12.3 \times 10^{-3}$ |
| ROD 2 | $22.1 \times 10^{-3}$ |
| ROD 3 | $15.6 \times 10^{-3}$ |
| ROD 4 (control) | $1.6 \times 10^{-3}$ |

We claim:

1. A method of qualitatively or quantitatively assaying a ligand selected from antigens and antibodies in a liquid sample which comprises the steps of:
   (a) contacting the sample with a predetermined quantity of a specific binding partner to the ligand, said specific binding partner being immobilized on an effective gate electrode of a field effect transistor, said gate electrode being spatially separate from the other components of the field effect transistor, said specific binding partner being an antibody or antigen capable of binding said ligand; and
   (b) determining whether a transistor characteristic selected from the group consisting of the drain current ($I_d$) and the gate electrode potential ($V_g$) is changed as a result of complex formation between said ligand and said specific binding partner, the other characteristic being maintained constant or variations therein compensated for, wherein a change in the drain current or the gate electrode potential is an indication of the presence of or quantity of said ligand.

2. A method as claimed in claim 1 wherein a transistor characteristic is changed as a result of complex formation between the ligand and the specific binding partner and is determined quantitatively.

3. A method as claimed in claim 1 or claim 2 wherein the initial rate of change of said transistor characteristic as a result of complex formation between the ligand and the specific binding partner is measured.

4. A method as claimed in claim 1 or claim 2 wherein an absolute change in said transistor characteristic is determined after the complexing reaction between the ligand and the specific-binding partner has been allowed to proceed for a controlled period of time.

5. A method as claimed in claim 1 or claim 2 wherein the drain potential $V_d$, the pH and ionic strength of the assay medium and the temperature of the system are maintained constant or variations therein compensated for.

6. Apparatus comprising a field effect transistor having an effective gate electrode on which a specific binding partner of a ligand to be assayed is immobilized, said gate electrode being spatially separate from the other components of the field effect transistor.

7. Apparatus as claimed in claim 6 wherein the said effective gate electrode is a titanium dioxide gate electrode.

8. Apparatus as claimed in claim 6 or claim 7 wherein said effective gate electrode is covered with a membrane which is either permeable to, or perm-selective for, the ligand under assay.

9. Apparatus as claimed in claim 6 which includes a reference electrode.

10. An apparatus as claimed in claim 9 wherein at least one of the effective gate electrode and the reference electrode is covered with a membrane which is either permeable to, or perm-selective for, the ligand under assay.

* * * * *